United States Patent [19]

Schaldach

[11] Patent Number: 5,344,386

[45] Date of Patent: Sep. 6, 1994

[54] STIMULATION SYSTEM FOR A SKELETAL MUSCLE

[75] Inventor: Max Schaldach, Erlangen, Fed. Rep. of Germany

[73] Assignee: Biotronik Mess- und Therapiegeräte GmbH & Co., Ingenierbüro Berlin, Berlin, Fed. Rep. of Germany

[21] Appl. No.: 943,306

[22] Filed: Sep. 14, 1992

[30] Foreign Application Priority Data

Sep. 12, 1991 [DE] Fed. Rep. of Germany ....... 4130596

[51] Int. Cl.$^5$ .............................................. A61M 1/10
[52] U.S. Cl. ........................................ 600/16; 607/48
[58] Field of Search ................... 128/419 R, 421, 422, 128/423 R; 600/16, 17, 18

[56] References Cited

U.S. PATENT DOCUMENTS

| | | | |
|---|---|---|---|
| 5,007,927 | 4/1991 | Badylak et al. | 600/16 |
| 5,069,680 | 12/1991 | Grandjean | 600/16 |

FOREIGN PATENT DOCUMENTS

| | | | |
|---|---|---|---|
| 9108006 | 6/1991 | World Int. Prop. O. | |
| 2006738 | 4/1992 | World Int. Prop. O. | 600/16 |

*Primary Examiner*—William E. Kamm
*Attorney, Agent, or Firm*—Spencer, Frank & Schneider

[57] ABSTRACT

A stimulation system for a skeletal muscle in a patient having a heart treated with cardiomyoplasty, for use as a supplement to a conventional cardiac pacemaker circuit, includes a stimulation unit for producing output signals to stimulate the skeletal muscle under control of the cardiac pacemaker circuit, and a plurality of implantable electrodes connected to the stimulation unit and the skeletal muscle, for selectively delivering output signals from the stimulation unit to the skeletal muscle. The stimulation unit output signal intensity is controlled by the cardiac pacemaker circuit to follow a value representative of the momentary physical stress and cardiovascular requirement, respectively. The value representative of the cardiovascular requirement includes an autonomous nervous system activity value which is substantially independent of further influential values.

19 Claims, 2 Drawing Sheets

STIMULATION SYSTEM FOR A SKELETAL MUSCLE

BACKGROUND OF THE INVENTION

1. Field of The Invention

The invention relates to a stimulation system of the type wherein a stimulation unit is connected to skeletal muscle by implantable electrodes and controlled by a pacemaker.

2. Background Information

Severe therapy resistant cardiac insufficiency — a significant problem because of its frequency of occurrence and mortality — can be treated with the technology of cardiomyoplasty.

In cardiac surgery there is generally a great demand for systems which are able to fully or partially take over the heart's pumping function. Cardiomyoplasty — this promising method which has been in clinical use since 1985 — is a technique for functionally replacing the loss of cardiac muscle tissue by skeletal muscles, particularly by the latissimus dorsi muscle (LDM). Surgical interventions are known to have been performed in cardiac patients to support heart contractions by placing a striated skeletal muscle of the patient's own body, preferably from the area of his back, completely or partially around the heart.

It is also known that this skeletal muscle can be trained by chronic electrostimulation for six weeks with low frequencies around 2 to 10 Hz whereupon it becomes relatively resistant to fatigue. The conversion of the muscle tissue, which is composed originally of types of muscle fibers, is here effected in such a way that the more fatigue resistant type is in the majority at the end of conditioning.

Stimulation systems have been developed which emit individual pulses in short succession (burst stimulators). Since the skeletal latissimus dorsi muscle (LDM) stimulated by an individual pulse reacts with a contraction that last about 70 ms, but the time period of the systole of the heart lasts 200 to 250 ms, the muscle contraction is electronically adapted to the time curve of the heart contraction. The duration of the contraction is then extended to correspond to the burst duration. Such a known implantable pacemaker is constructed of two channels, with each channel including a receiving unit, a synchronizing unit and an output unit.

The drawback in the prior art system is the fact that the stimulation is always effected with constant values and is thus not adapted to the momentary physical stress.

SUMMARY OF THE INVENTION

It is thus the object of the invention to stimulate a skeletal muscle (latissimus dorsi muscle) employed to support the heart muscle so that it is able to perform the same function as the heart muscle.

This is accomplished by controlling stimulation intensity to follow value representative of momentary physical stress and cardiovascular requirement.

The invention is based on the realization that it is not only the escape sequence derived from the sensor output signal and/or from the heart rhythm but also the stimulation intensity that must be closely adapted to the actual, momentary physiological demands of the patient. In this connection, the stimulation of the skeletal muscle must be adapted to the particular type of stimulation conduction.

According to the invention, a stimulation system is provided for a skeletal muscle that has been placed around the patient's heart to additionally support cardiac contractions, wherein the stimulation pulses are derived from the output signals of a suitable physiological cardiac pacemaker and correspond to the patient's actual, momentary physiological requirements.

This involves, in particular, the detection of the state of the autonomous (vegetative) nervous system and information derived therefrom to stimulate, excite and activate the skeletal muscle employed to support the heart muscle in such a graduated manner that it is tuned to the physiological requirements of the total organism in a hemodynamic and metabolic respect.

In an advantageous manner, the skeletal muscle is stimulated by an electrical pulse generator which provides a series of pulses whose stimulating parameters are set in the manner to be described below by values that are directly or indirectly derived from the state of the autonomous nervous system.

The charging of the electrodes connected with the skeletal muscle is effected by way of the stimulation unit and by the pacemaker, on the one hand, at a certain automatically adjustable rate R of the stimulation pulses and, on the other hand, corresponding to a value representative of the momentary physical stress and the cardiovascular requirement, by means of a stimulation power, particularly amplitude and duration, and/or by means of a variable number of electrodes that are actuated in each case.

If the heart's own rhythm is correct, the value representative of the momentary physical stress and the cardiovascular requirement is formed by the body's heart rate.

If the heart's own rhythm is absent, stimulation pulses of a defined rate are generated by the cardiac pacemaker.

If the heart rate exceeds a certain programmable value, the ratio of cardiac action to muscle contraction is changed and the pulse power applied to the electrodes is increased. As a function of the value representative of the momentary physical stress or the cardiovascular requirement, the rate is stepped down at a ratio to the natural rhythm or, if there is no natural rhythm, to the rhythm stimulated by the conventional pacemaker to a degree depending on this stress, with the reduction ratio decreasing with increasing physical stress or cardiovascular requirement until the ratio of 1:1 is reached.

On the part of the cardiac pacemaker, the value representative of the momentary physical stress is generated, if the heart's own rhythm is absent, from a sensor signal for the patient's activity or from a secondary value representing the stress on the circulatory system, such as the temperature of the blood, the oxygen saturation of the blood or the pH value of the blood.

A further physiological check of the stimulation intensity can be effected with a value that is a direct measure of the internal cardiovascular requirement for heart output and not — as the pacemakers controlled by the patient—s activity — a value derived from the output requirement by way of an external parameter.

An analysis of circulation hemodynamics indicates that cardiovascular output can be described sufficiently in the form of a (negative feedback controlled) system. The average arterial blood pressure is the controlled value and the cardiac output requirement is the controlling variable. Under physiological conditions, the short-term control of the average arterial blood pressure works well. All demands on the cardiovascular system are held in equilibrium and therefore furnish reliable perfusion of the tissue.

Most demands on the cardiovascular system influence the peripheral vascular resistance. The most relevant of these demands are: physical activity, skin temperature and the core temperature of the body, the acid level, the equilibrium and body posture. One of the demands influences the resistive as well as the capacitive characteristics of the periphery by changing the constriction of the arterioles or venules. The secondary effects are changes in vascular resistance, in blood pressure, in venal return flow and in cardiac output. For example, vascular resistance may change five fold during physical activity. To keep the blood pressure constant, venal return flow and cardiac output must be changed correspondingly in the opposite direction.

Cardiac output requirement is the controlling value. It is the product of the heart rate and stroke volume.

Changes in cardiac output requirement are in an inverse relationship to the changes in vascular resistance with the result that the average arterial blood pressure is held essentially constant. Under physiological conditions, the adaptation of the cardiac output requirement to the changes in vascular resistance is effected by a (closed loop feedback) system including baroreceptors operating as pressure sensors in the aortal arc and in the carotid sinus. The output signals of these baroreceptors are fed to the medullar cardiovascular centers. These centers send output signals to the heart by way of the sympathetic or the parasympathetic nervous system.

The sympathetic nervous system regulates the sine frequency and the ventricular stroke volume. The parasympathetic nervous system, in contrast, influences primarily the heart rate. The combination of chronotropic and inotropic factors together lead to a control of the cardiac output. Other variables which influence the heart on the basis of the same external paths are, among others: pain, emotion and physiological stress.

In patients suffering from chronotropic insufficiency, the feedback mechanism with which the heart rate is regulated by way of the sinoatrial node is interrupted. As a consequence, these patients are able to react to stress only by a change in the stroke volume. However, the possible change in the stroke volume is very slight during physical activity.

The chronotropic component in the cardiac output reserve can be restored in that the natural stimulation device is replaced by an artificial one.

Stimulation theory offers several different strategies for counteracting the influence of stress on the circulatory system:

(1) open-loop control is employed in many frequency adaptive cardiac pacemakers;
(2) output demand is related to stress in that the cardiac output is adapted to the calculated output requirement; temperature and breathing controlled cardiac pacemakers belong to this category;
(3) physiologically controlled in which the measured signal directly reflects the circulatory system requirements.

A central, easily reproducible value decisive for cardiovascular requirements and furnished by the autonomous nervous system (ANS) is the regionally operative increase (ROI) of the intracardial impedance of the right ventricle. The interval in which the change is generally the greatest during isovolumetric contraction and here again the region exhibiting the greatest change during changes in stress on the patient are selected with preference. Thus, the determined signal has useful characteristics which result in it being preferably suitable as a control signal for the parameters of the cardiac pacemaker that determine cardiac output.

The regionally operative increase is inversely proportional to myocardial contractility. The greater the contractility, the faster it must be possible to build up the pressure required to open the ventricular valves of the heart.

The ANS here provides autonomous nerve information that is substantially independent of further influential values and is representative of the cardiac output requirement. It exhibits an inotropic behavior indicative of cardiovascular requirements as a control signal for the re-establishment of chronotropic behavior and constitutes a value that is decisive for the modulation of contractility.

In particular, ventricular contractility is under sympathetic control. Since the pre-injection phase is related to contractility, changes in the ANS can be employed to monitor changes in the sympathetic tonus.

Since the contractility of the left ventricle is part of the region of the circulatory system that is under higher pressure, the ANS is defined with respect to this chamber. However, the right ventricle is better suited for intracardial measurements of the ANS.

ANS signals measured in the right and left ventricle during physical activity exhibit an excellent relationship to one another, although the ANS signals from the left ventricle are slightly longer than the ANS signals from the right ventricle.

The task of constructing a cardiac pacemaker that employs ANS signals as its control signals, is converted to the task of being able to measure an ANS related value with sufficient accuracy. One method is based on intracardial impedance measurements. It has been found that the intraventricular volume can be measured by way of the impedance. These measurements were made with an arrangement of multiple electrodes in the respective ventricle. It is not necessary to measure the absolute value of the volume in order to determine the end of the ANS signals. It is sufficient to determine the point in time at which the volume begins to change. It has been found that sufficient resolution can be attained with a unipolar electrode that is disposed in the ventricle, in which case the cardiac pacemaker housing serves as the counter-electrode.

Thus, the value representative of cardiovascular requirements is an autonomous nervous system information that is substantially independent of further influential values. This information is obtained by impedance plethysmography. The autonomous nervous system information is a regionally operative increase in conductivity in the right ventricle, particularly in the region of maximum conductivity change during isovolumetric contraction, with this region being selected by means of a time window. Preferred is a region in which a maximum conductivity change can be determined upon a change in stress.

BRIEF DESCRIPTION OF THE DRAWINGS

Advantageous features of the invention are defined in the dependent claims and will be described in greater detail below together with a description of the preferred embodiment of the invention and with reference to the drawing figures, in which:

DETAILED DESCRIPTION OF THE PREFERRED EMBODIMENTS

Figure 1:
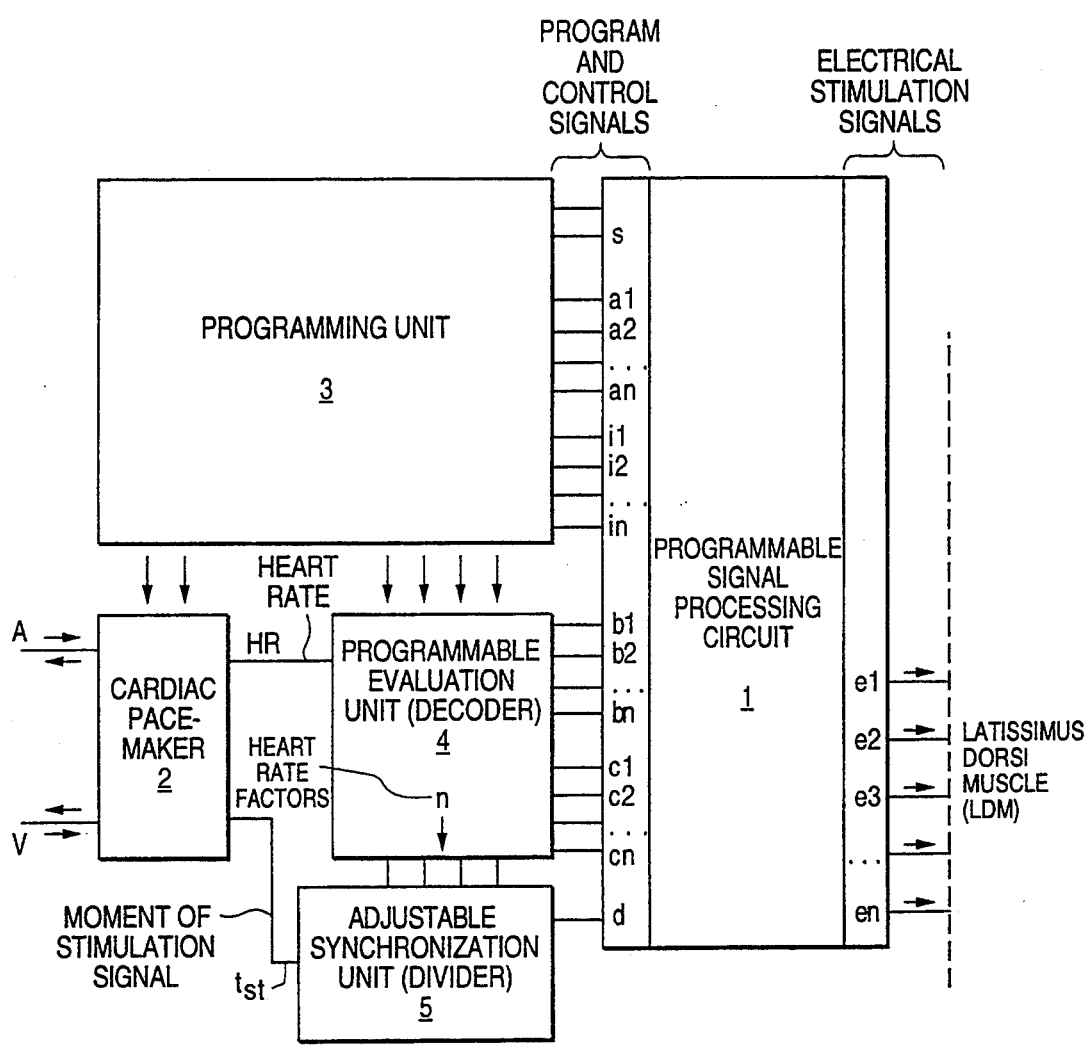
FIG. 1 is a block circuit diagram of an advantageous embodiment of the stimulation system according to the invention.

In the stimulation system according to the invention —shown in FIG. 1 — a signal processing circuit 1 generates stimulation pulses which are detected from the output signals HR and $t_{st}$ of a cardiac pacemaker 2. The output signal for the heart rate HR is here fed to a programmable evaluation unit 4 which is configured, in particular, as a decoder, and the output signal for the moment of stimulation $t_{st}$ is fed to an adjustable synchronization unit 5 which is configured, in particular, as a divider. Additionally, a programming unit 3 is connected with cardiac pacemaker 2, with decoder 4 and with signal processing circuit 1, each being programmable and having appropriate programming inputs. A control unit 6 (FIG. 2) turns signal processing circuit 1 on and off.

The value representative of the momentary physical stress and the cardiovascular requirement, respectively, if the heart's own rhythm is in order, is formed by its heart rate HR and, if the heart's own rhythm is absent, by a heart rate HR generated by the cardiac pacemaker 2.

The programmable decoder 4 permits the derivation of different factors n from the heart rate HR. A division by the factor n=1 here corresponds, for example, to the control known as the Medtronic synchronous pacemaker or to stimulation initiated by a natural signal, respectively. As a function of the value HR representative of the momentary physical stress or cardiovascular requirement, the heart rate is stepped down at a ratio, that is a function of this stress, to the natural rhythm — or if there is no natural rhythm — to the rhythm stimulated by the conventional pacemaker, with the reduction ratio decreasing with increasing physical stress and cardiovascular requirement, respectively, to a ratio of 1:1.

According to the invention, decoder 4 is provided with outputs for selecting and actuating the electrodes with the necessary power.

Figure 2:
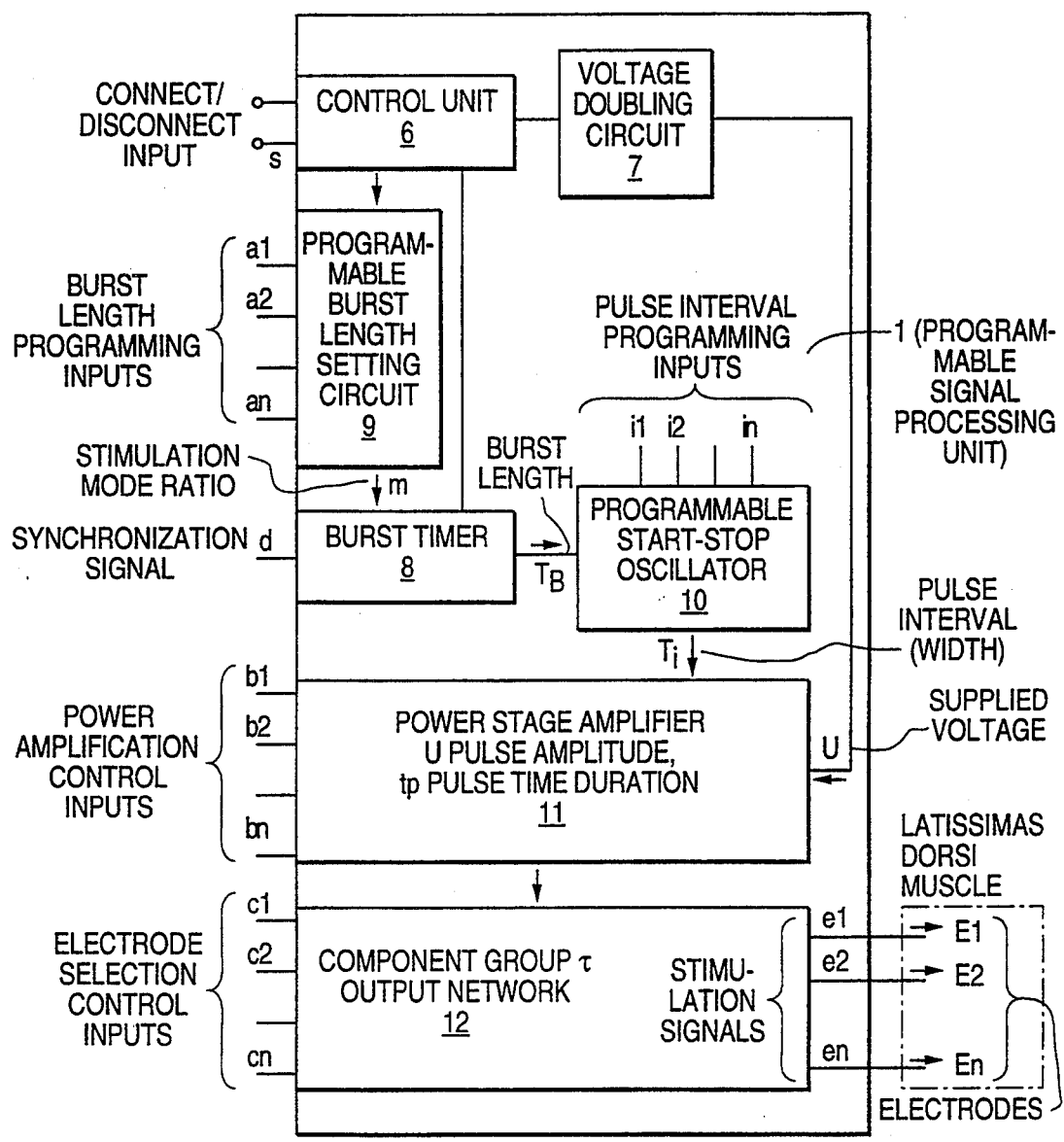
FIG. 2 is a block circuit diagram of the signal processing circuit of the system of FIG. 1.

The programmable signal processing circuit 1 according to the invention is shown in the block circuit diagram according to FIG. 2.

The control unit 6, which can be turned on and off, is connected, on the one hand, with a voltage doubling circuit 7 and, on the other hand, directly and indirectly by way of a circuit equipped with programming inputs $a_1$ to $a_n$ for setting the burst length 9 by means of a burst timer 8. When actuated by the divider, the burst timer 8 counts five to eight pulses according to the preset burst length $T_B$. These pulses output by the divider 5 and required to generate a burst duration $T_B$ that is synchronized with the heart stimulation are synchronized by the triggering pulse output by the cardiac pacemaker 2 at stimulation moment $t_{st}$ and are present at at least one input d of burst timer 8.

The output of burst timer 8 is connected with the control input of a programmable start-stop oscillator 10 which emits, corresponding to the stimulation mode set by burst length setting circuit 9, that is, during the burst duration $T_B$, short pulses having a time duration of $T_p=0.2$ to 1 ms at an excitation frequency $f=15$ to 40 Hz. A change in the pulse interval $T_i=1/f$ by way of programming inputs $i_l$ to $i_n$ that are connected with programming unit 3 influences the contraction force by way of a change in the excitation rate and thus also a change in the force generated by an individual motor unit (temporal summation).

Voltage doubling circuit 7 preferably generates $-5.6$ V as the operating voltage for a power stage 11 from the supply voltage Us=2.8 V of existing suitable pacemakers. This power stage 11 amplifies the power of the output pulses of start-stop oscillator 10 as a function of the automatic programmable setting effected by way of control inputs $b_1$ to $b_n$. For this purpose, control inputs $b_1$ to $b_n$ are connected with the corresponding outputs of the programmable decoder 4. With increased activity, the heart is increasingly supported by the skeletal muscle since an increase in the pulse width $T_i$ and/or the pulse amplitude U amplifies the contraction force of the muscle by way of an increase in the activated motor units (spatial recruitment).

Control inputs $c_1$ to $c_n$ of a component group 12 connected with power stage 11 for the selection of at least one electrode $E_1$ to $E_n$ to be connected to its output with a defined time delay are also connected with corresponding outputs of programmable decoder 4. Thus, a comparable stimulation line present in the heart can be simulated in the skeletal muscle and/or, if actuated simultaneously, the stimulation intensity can be increased. For each electrode $E_1$ to $E_n$ an output network including a protective circuit is provided in component group 12.

The electrical signals from the heart are received by a sensor electrode, not shown in FIG. 1, which is disposed intramurally in the wall of the right ventricle and, if required, if the heart rate drops below a programmed value, the heart muscle is stimulated by way of the same electrode.

If, however, the heart rate exceeds a certain preprogrammed value, the electrodes of the muscle stimulation channel are activated — possibly after the expiration of a programmed delay period — in order to put out a burst pulse for the latissimus dorsi muscle (LDM) by way of at least two electrodes. The burst duration $T_B$ determines the duration of the contraction of the muscle.

As soon as, the heart rate exceeds a further pre-programmed value, however, the ratio of cardiac action to the number of muscle stimulations is automatically changed, with the stimulation mode m remaining the same. The ratio m of heart contractions to muscle contractions is a function of the value set by way of the programmable burst length setting circuit 9.

The electrodes of each muscle stimulation channel are composed of a flexible platinum/iridium nitride coated wire provided with a silicone insulation that is arranged outside the muscle in such a way that no conductive electrode components remain outside the muscle. They may be positioned perineural preferably, however, intramuscular in the direct proximity of the nerve branches in that a non-resorbable thread fastened to the distal end of each electrode and equipped with a bent needle provided to pierce the muscle is pulled through the muscle. Once the electrode has been put in place, the insulation is pushed up to the muscle epimysium and is fixed there. An electrode serving as cathode is placed in the region of the proximal branch of the nerve to the latissimus dorsi muscle (LDM) and the electrode serving as anode a few centimeters distal thereof.

By means of programming unit 3 it is possible to indirectly change, by associating a factor n with the representative heart rate HR, the number of individual pulses within a burst and the stimulation mode, respectively, the pulse interval $T_i = 1/f$ where $f = 15$ to 40 Hz, and the burst duration $T_B$ as well as the power by way of the pulse amplitude U and/or the pulse width $t_p$. Preferably, the following parameters are set for standard stimulation: pulse width $T_p = 210$ μs, pulse interval $T_i = 30$ ms, pulse amplitude $U = 5$ V, burst duration $T_B = 185$ ms for a stimulation mode of 1:1 to 1:8.

The present invention is not limited in its embodiments to the above-described preferred embodiment. Rather, a number of variations are conceivable which take advantage of the described solution even for basically different configurations.

I claim:

1. A stimulation system for stimulating a skeletal muscle in the body of a patient having a heart treated with cardiomyoplasty, for use as a supplement to a conventional cardiac pacemaker, the skeletal muscle being surgically prepared from the body of the patient, the stimulation system comprising:

stimulation means for producing output signals to stimulate the skeletal muscle, the stimulation means including an input connected to an output of the cardiac pacemaker and being controlled by the cardiac pacemaker, and a plurality of implantable electrodes connected to the stimulation means and the skeletal muscle, for selectively delivering output signals from the stimulation means to the skeletal muscle, wherein the cardiac pacemaker outputs a signal to control the stimulation means output signal intensity to respond to the momentary physical stress and cardiovascular requirement, respectively, of the patient, wherein at least one heart and/or body sensor is provided to sense the momentary physical stress and cardiovascular requirement of the patient, the at least one sensor having an output connected to an input of the cardiac pacemaker or to the input of the stimulation means, and wherein the at least one sensor sensing the cardiovascular requirement delivers an autonomous nervous system activity value which is independent of further influential values.

2. A stimulation system according to claim 1, wherein the stimulation means includes switching means for switching the output of the stimulation means, and control means connected to the switching means, for receiving a selection signal from the cardiac pacemaker and controlling the switching means based thereon, and wherein the stimulation means output signal is controlled by the cardiac pacemaker to respond to the momentary physical stress and the cardiovascular requirement, respectively, by controlling at least one of the following parameters of the stimulation means output signal: a rate of the stimulation means output signal, an amplitude of the stimulation means output signal, and a duration of the stimulation means output signal, and by controlling the number of electrodes selected to deliver the output signal from the stimulation means to the skeletal muscle in each case, the controlling of the number of electrodes being effected by the switching means, the switching means connecting the output of the stimulation means with different ones of the electrodes based on the selection signal received by the control means.

3. A stimulation system according to claim 2, wherein one of the at least one heart and/or body sensors for sensing the momentary physical stress and the cardiovascular requirement, respectively, is a sensor for sensing the patient's heart rate.

4. A stimulation system according to claim 3, wherein programmable evaluation means is provided connected with the at least one heart and/or body sensor to step down the rate of the stimulation means output in dependence on the output signal of the at least one sensor being a measure of the momentary physical stress or the cardiovascular requirement in a reduction ratio dependent on this stress to the natural rhythm of the patient's heart, or, to a rhythm stimulated by the conventional pacemaker, with the reduction ratio being programmed as decreasing with increasing physical stress and cardiovascular requirement, respectively, to a ratio of 1:1.

5. A stimulation system according to claim 3, wherein for sensing the momentary physical stress a sensor is provided for the patient's activity or a secondary value representative of stress on the circulatory system, the secondary value including at least one of:

the temperature of the blood, the oxygen saturation of the blood, or the pH value of the blood.

6. A stimulation system according to claim 1, wherein the at least one sensor delivering autonomous nervous system information a sensor for detecting a regionally operative increase in conductivity in the right ventricle of the patient's heart.

7. A stimulation system according to claim 6, wherein the sensor for detecting the regionally operative increase in conductivity in the right ventricle of the patient's heart is actuated in a time region of a maximum change in conductivity during isovolumetric contraction.

8. A stimulation system according to claim 7, wherein means for selecting a time window is provided for effecting measurements of the regionally operative increase in conductivity in the right ventricle of the patient's heart, the time window being placed into a time region in which a maximum change in conductivity can be noted under different stresses, this time region being predetermined in accordance with previous measurements.

9. A stimulation system according to claim 1, further comprising:

programmable evaluation means including at least one control output;

adjustable synchronizing means; and programmable signal processing means connected by said programmable evaluation means and by said adjustable synchronizing means to outputs of the cardiac pacemaker;

wherein the stimulation means output signals comprise stimulation pulses derived from the output signals of the cardiac pacemaker, the stimulation pulses being generated for at least two of the plurality of implantable electrodes in the skeletal muscle; and wherein stimulation effective parameters of said stimulation pulses, including a pulse width and a pulse amplitude, and a given pulse interval and a burst duration are set together with a stimulation mode by the programmable evaluation means, wherein pulse width and pulse amplitude are evaluated on the basis of the actual heart rate, that is derived directly or indirectly from the signal of the sensor delivering the autonomous nervous system information.

10. A stimulation system according to claim 9, further comprising:
programming means;
wherein the programmable signal processing means is connected with said programming means and the programmable signal processing means includes:
connectable/disconnectable control means;
voltage doubling means connected to the connectable/disconnectable control means;
a programmable circuit having an input connected with the at least one sensor sensing the cardiovascular requirement and having programming inputs, for setting a burst length, the programmable circuit being connected to the connectable/disconnectable control means and programmable by the programming means by way of said programming inputs;
a burst timer which is connected with the programmable circuit for setting the burst length and to the connectable/disconnectable control means, including at least one control input;
a programmable start-stop oscillator connected to the burst timer, including including a programming input connected to the programming means; and
a programmable power stage that is connected with the voltage doubling means and to the programmable start-stop oscillator, including a programming input connected to the programming means;
wherein a ratio of heart action to the stimulation means output pulse rate is evaluated by and is output from said programmable circuit for setting the burst length to said burst timer, and is adjustable to a programmed ratio by said programmable circuit for setting the burst length under control of the programming means by way of said programming inputs;
wherein the adjustable synchronizing means is connected to at least one input of the burst timer for synchronizing said burst timer and is charged by the programmable evaluation means so that a burst pulse is generated as soon as the rate of the heart action being sensed by the at least one sensor exceeds a first predefined heart rate HR; and
wherein, if the rate of the heart action or heart rate HR, respectively, exceeds a second, predefined value, the ratio of heart action to the stimulation means output pulse rate is changed by way of a programmed number output by the programmable evaluation means to the adjustable synchronizing means.

11. A stimulation system according to claim 10, wherein the burst timer includes an output which is connected with the control input of the start-stop oscillator which, during a burst duration, emits short pulses corresponding to a stimulation mode given by the programmable evaluation means and the programmable circuit for setting the burst length, of a time duration of $T_p = 0.2$ to $1$ ms at a stimulation means output pulse rate or an excitation frequency, respectively, $f = 15$ to $40$ Hz; and
wherein a change in the pulse interval $T_i = 1/f$ can be effected by way of sending programming signals to the programming inputs of the programmable start-stop oscillator from the programming means.

12. A stimulation system according to claim 10, wherein the programmable evaluation means is connected to at least one control input of said programmable power stage for amplifying power of the output pulses of the start-stop oscillator as a function of a setting that is effected automatically by way of sending programming signals to said at least one control input from the programming means.

13. A stimulation system according to claim 10, further comprising a component group output network, including switches, connected to the programmable power stage;
wherein control inputs are provided for said component group output network for the switches thereof to effect selection of at least one electrode to be connected to an output of the component group output network with a programmed time delay, said control inputs being connected with at least one of the control outputs of the programmable evaluation means.

14. A stimulation system according to claim 13 wherein said component group output network further includes an output network including a protective circuit for each electrode.

15. A stimulation system according to claim 10, wherein a number of individual stimulation pulses within a burst and a stimulation mode, respectively, a stimulation pulse interval $T_i = 1/f$, where $f = 15$ to $40$ Hz, and a burst duration can be changed indirectly by the programming means by associating a factor to a representative heart rate and wherein the stimulation pulses output can be changed by way of the pulse amplitude and/or the pulse width.

16. A stimulation system according to claim 9, wherein the electrodes include a distal end, comprise a flexible wire coated with platinum/iridium nitride, and are provided with a polyurethane insulation arranged outside the skeletal muscle, and
wherein a non-resorbable thread having a bent needle is provided to pierce the skeletal muscle and is fastened to the distal end of each electrode.

17. A stimulation system according to claim 1, wherein the programmable evaluation means comprises a decoder having at least one output and the adjustable synchronization means comprises a divider having at least one input, the decoder being connected to the divider by at least one respective decoder output and divider input.

18. An apparatus for stimulating a surgically prepared skeletal muscle of a patient coupled to a human heart of the patient, the skeletal muscle functionally replacing lost cardiac muscle, the patient having a pacemaker, the apparatus comprising:
a plurality of electrodes implanted in the surgically prepared skeletal muscle coupled to the human heart of the patient;
programmable signal processing means, coupled to the plurality of electrodes, for generating and outputting electrical stimulation pulses;
a programmable evaluation unit coupled to the pacemaker for receiving a signal representative of a heart rate of the patient, and coupled to the programmable signal processing means for providing stimulation pulse power control and electrode selection settings thereto, and for generating heart rate division factors;

adjustable synchronization means, coupled to the programmable evaluation unit for receiving the heart rate division factors therefrom, coupled to the pacemaker for receiving a moment of stimulation signal therefrom, and coupled to the programmable signal processing means for providing a synchronization signal thereto in accordance with the heart rate division factors and the moment of stimulation signal; and a programming unit, coupled to the pacemaker and to the programmable evaluation unit for providing respective programming settings thereto, and coupled to the programmable signal processing means for providing burst length settings, pulse interval settings, and connect/disconnect control settings thereto;

wherein said programmable signal processing means comprises:

output means, coupled to the programmable evaluation unit for receiving the electrode selection settings therefrom, and coupled to the plurality of electrodes, for selectively providing the electrical stimulation pulses to the electrodes in response to the electrode selection settings;

power stage means, coupled to the programmable evaluation unit for receiving the stimulation pulse power control signals therefrom, and coupled to the output means, for providing the electrical stimulation pulses thereto, the pulse duration and/or the pulse amplitude of the electrical stimulation pulses being controlled by the stimulation pulse power control signals and a pulse interval signal;

a programmable start-stop oscillator, coupled to the programming unit for receiving the pulse interval settings therefrom, and coupled to the power stage means, for providing the pulse interval signal thereto in accordance with the pulse interval settings and a burst length signal;

a burst timer, coupled to the adjustable synchronization means, for receiving the synchronization signal therefrom, and to the programmable start-stop oscillator for providing the burst length signal thereto in accordance with the synchronization signal and a stimulation mode ratio;

programmable burst length means, coupled to the programming unit for receiving the burst length settings therefrom, and to the burst timer for providing the stimulation mode ratio thereto;

voltage doubling means for providing a voltage to the power stage means to use in producing the electrical stimulation pulses; and control means, coupled to the programming unit for receiving the connect/disconnect control setting therefrom, and coupled to control the voltage doubling means, the programmable burst length means, and the burst timer.

19. An apparatus according to claim 18, wherein the programmable evaluation unit comprises a decoder having an output, and wherein the adjustable synchronization means comprises a divider having an input, the decoder and the divider being connected together by the respective input and output.

* * * * *